US00PP27514P3

(12) United States Plant Patent
O'Connell

(10) Patent No.: US PP27,514 P3
(45) Date of Patent: Dec. 27, 2016

(54) ***ECHEVERIA* PLANT NAMED 'SAHARA'**

(50) Latin Name: ***Echeveria* hybrid**
Varietal Denomination: Sahara

(71) Applicant: Renee O'Connell, Escondido, CA (US)

(72) Inventor: Renee O'Connell, Escondido, CA (US)

(73) Assignee: Altman Plants, Vista, CA (US)

( * ) Notice: Subject to any disclaimer, the term of this patent is extended or adjusted under 35 U.S.C. 154(b) by 80 days.

(21) Appl. No.: 14/544,914

(22) Filed: Mar. 6, 2015

(65) Prior Publication Data

US 2016/0270278 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and distinct *Echeveria* cultivar named 'Sahara' is disclosed, characterized by excellent resistance to stressors, including excellent resistance to both heat and cold and constant exposure to the sun, making it an excellent landscape plant. The new cultivar displays enhanced disease resistance as compared to other *Echeverias*, in particular to the pathogens *Rhizoctonia, Fusarium,* and Powdery Mildew. *Echeveria* 'Sahara' is more easily and rapidly propagated due to robust growth and enhanced resistance to stressors. In addition, the new cultivar 'Sahara' offsets profusely, quickly forming clumps, enabling increased and faster propagation. The new cultivar produces larger flowers, compared to many other *Echeveria* cultivars. The new variety is an *Echeveria*, part of the Crassulaceae complex that includes *Pachyphytum, Graptopetalum, Sedum* and others. *Echeveria* is a popular genus, typically produced as container plants or landscape plants.

2 Drawing Sheets

Figure 1:
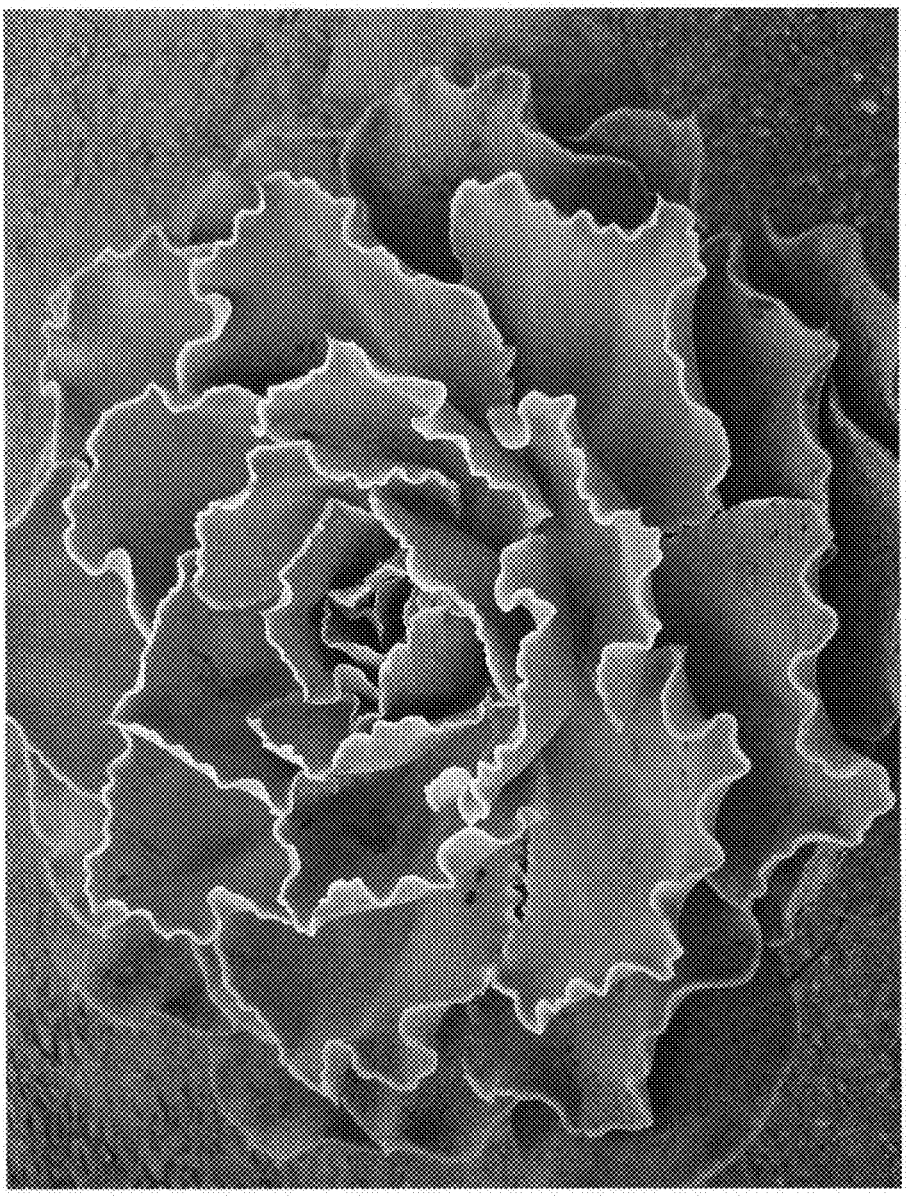

Latin name of the genus and species: *Echeveria* hybrid.
Variety denomination: 'SAHARA'.

BACKGROUND OF THE INVENTION

The new *Echeveria* cultivar is the product of a planned breeding program. The new variety originated from a cross pollination of the proprietary, unpatented, seed parent, *Echeveria* 'B71-J2' with the pollen parent an unpatented, proprietary variety of *Echeveria* referred to as '13-17.' The cross pollination was made during April of 2010 in Vista, Calif., at a commercial greenhouse. The new cultivar 'Sahara' was discovered and selected by the inventor, Renee O'Connell, in March of 2011, in Vista, Calif. at a commercial greenhouse.

The seed parent is the, unpatented, proprietary variety referred to as *Echeveria* 'B71-J2'. The pollen parent is the unpatented, propriety variety referred to as *Echeveria* '13-17'. The new variety was discovered in March of 2011 by the inventor in a group of seedlings resulting from the 2010 crossing, in a commercial greenhouse in Vista, Calif.

Asexual reproduction of the new cultivar 'Sahara' was first performed in Vista, Calif., at a commercial greenhouse, by vegetative cuttings in May of 2011. 'Sahara' has since produced multiple generations and has shown that the unique features of this cultivar are stable and reproduced true to type.

SUMMARY OF THE INVENTION

The cultivar 'SAHARA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SAHARA' These characteristics in combination distinguish 'SAHARA' as a new and distinct *Echeveria* cultivar:

1. Exhibits excellent heat and sun resistance not shown by other comparable *Echeveria* varieties.
2. Exhibits excellent cold resistance not shown by other comparable *Echeveria* varieties.
3. Exhibits the rare combination of heat and cold resistance, not observed in other comparable *Echeveria* cultivars.
4. Much more easily and rapidly propagated due to robust growth and enhanced resistance to environmental stress.
5. Exhibits enhanced disease resistance, in particular, to the diseases *Rhizoctonia, Fusarium* and Powdery Mildew.
6. Larger flowers than most comparable *Echeveria.*
7. Freely offsetting, allowing for increased and more rapid propagation.

Plants of the new cultivar 'SAHARA' are similar to plants of the seed parent, *Echeveria* 'B71-J2' in most horticultural characteristics, however, plants of the new cultivar 'SAHARA' differ in the following;

1. Greater cold and heat tolerance.
2. Much larger flowers.
3. Greater disease resistant.
4. More prolific growth, enhancing cutting production.

Plants of the new cultivar 'SAHARA' are similar to plants of the pollen parent, *Echeveria* '13-17' in most horticultural characteristics, however, plants of the new cultivar 'SAHARA' differs in the following;

1. More attractive rosette, as it exhibits more marginal crenulation.
2. Greater disease resistance; particularly resistant to powdery mildew.
3. More prolific growth, enhancing cutting production and creating an attractive large cluster.
4. Much larger, not uncommon for the cluster to measure 14" or more in diameter.

COMMERCIAL COMPARISON

Plants of the new cultivar 'SAHARA' are comparable to the unpatented, commercial variety *Echeveria* 'Afterglow'. The two *Echeveria* varieties are similar in most horticultural characteristics; however, the new variety 'SAHARA' differs in the following:

1. Forms a more concentric rosette than does *Echeveria* 'Afterglow', producing a more aesthetically uniform rosette plant form.
2. Offsets more profusely than *Echeveria* 'Afterglow' , increasing the propagation rate, and producing a morphologically aesthetic cluster.

Plants of the new cultivar 'SAHARA' can also be comparable to the unpatented commercial variety *Echeveria* 'Imbricata'. The two *Echeveria* varieties are similar in most horticultural characteristics; however, the new variety 'SAHARA' differs in the following:

1. Superior heat and cold tolerance.
2. Greater disease resistance, in particular to the diseases *Fusarium, Rhizoctonia* and Powdery Mildew.
3. More adaptable to a wider set of environmental stressors, such as cold, heat, drought, and has greater longevity in the landscape environment.

BRIEF DESCRIPTION OF THE PHOTOGRAPHS

The accompanying photograph in FIG. 1 shows in full color the rosette of the new cultivar 'Sahara'.

Figure 2:
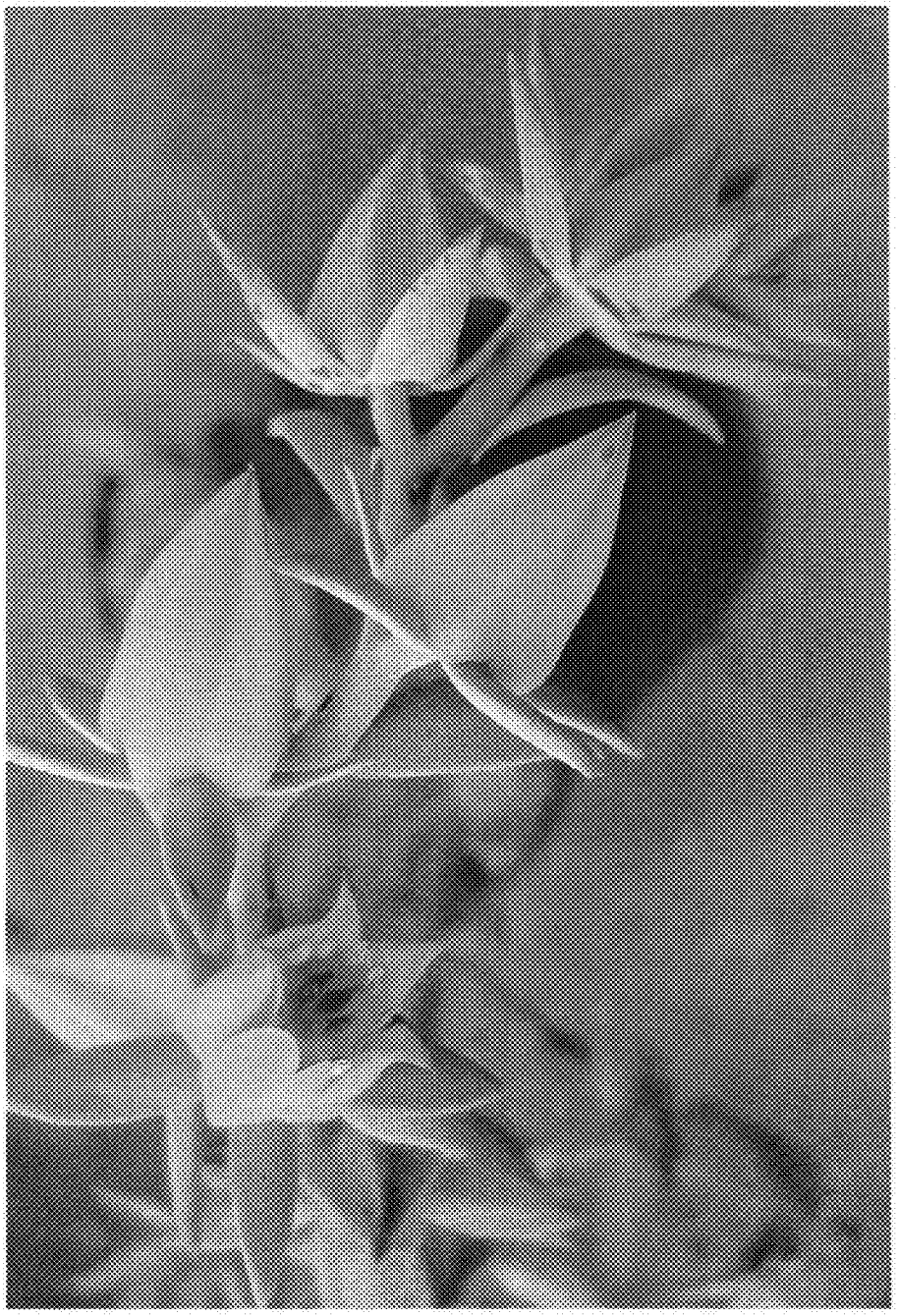

FIG. 2 shows in full color the inflorescence of the new cultivar 'Sahara'. Age of the plant photographed is approximately 14 weeks from a well rooted plantlet.

The photographs were taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Sahara' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'SAHARA'.

PROPAGATION

Type of propagation typically used: Terminal vegetative divisions.

Time to initiate roots: About 15 days at approximately 21° C.

Root description: Fibrous.

PLANT

Age of plant described: Approximately 6 months.

Container size of the plant described: 19 cm.

Growth habit: Densely rosulate, sessile.

Height: Approximately 10.7 cm to top of highest leaf. Approximately 57 cm to the top of the highest inflorescence.

Plant spread: 23 cm.

Growth rate: Moderately fast.

Branching characteristics: Freely offsetting when older.

FOLIAGE

Leaf:

*Arrangement*.—Rosulate.

*Average length*.—Approximately 10.9 cm.

*Longest length*.—Approximately 13.2 cm.

*Widest width*.—Approximately 8.5 cm.

*Width at base*.—2.2 cm.

*Shape of blade*.—Obovate.

*Apex*.—Mucronate.

*Base*.—Cuneate.

*Margin*.—Slightly undulate.

*Texture of top surface*.—Glabrous, somewhat glaucous.

*Texture of bottom surface*.—Glabrous, glaucous.

*Quantity of leaves per plant*.—Approximately 44.

*Color*.—Young foliage upper side, middle of leaf: Near P 126-12 U Pantone. Young foliage, upper side, if glaucous covering is removed: Near P 144-12 U Pantone. Young foliage upper side, apex: Near P 126-12 U Pantone. Young foliage, upper side, base: Near P 64-2 U Pantone. Young foliage, upper side, margin: Near P 151-1 U Pantone. Young foliage, upper side, margin near apex: Near P 58-10 U Pantone. Young foliage, under side: Near P 126-1 U Pantone. Young foliage underside, if glaucous covering is removed: Near P 168-16 U Pantone. Young foliage under side, apex: Near P 68-2 Pantone. Young foliage, under side, apical margin: Near P68-2 Pantone. Young foliage, under side, base: Near P 160-2 U Pantone. Mature foliage upper side: Near P 176-5 U Pantone. Mature foliage upper side, apex: Near P 178-12 U Pantone. Mature foliage, upper side, near base: Near P 159-10 U Pantone. Mature foliage upper side, margin: Near P 52-13 U Pantone. Mature foliage, upper side, margin, near apex: Near P 178-41 U Pantone. Mature foliage, upper side, apical margin: Near P 62-5 U Pantone. Mature foliage, upper side, margin, near base: Near P 160-1 U Pantone. Mature foliage, under side: Near P 78-5 U Pantone. Mature foliage, under side, apex: Near P 178-11 U Pantone. Mature foliage, under side, near base: Near P 159-3 U Pantone. Mature foliage, under side, margin: Near P 52-13 U Pantone. Venation: There is no visual appearance of venation.

FLOWER

Natural flowering season: Spring, Autumn.

Inflorescence type and habit: Cyme with 4 cincinni.

Rate of flower opening: 1 flower opens every 2-3 days, depending upon ambient conditions.

Flower longevity on plant: 2-3 days, depending upon ambient conditions.

Quantity of flowers: 27.

*Total inflorescence size*.—Height: Approximately 57 cm. Width: Approximately 26 cm.

*Corolla*.—Arrangement: Actinomorphic. Size: Length: Approximately 2.3 cm. Width: Approximately 1.4 cm at widest point. Lobe Length: Approximately 22 mm. Lobe width: Approximately 6 mm. Margin: Entire. Shape: Pentagonally campanulate. Apex: Acute. Texture: Glabrous. Color: Outer surface, near base: Near P 62-15 U Pantone. Outer surface, apex: Near P 65-13 U Pantone. Inner surface, near base: P 68-6 U Pantone. Inner surface, apex: Near P 59-10 U Pantone. Inner surface, apex: Near P 59-7 U Pantone. Petal Color: When opening: Petal color, outer surface: Near P 79-10-U Pantone. Petal color, outside tip: P 79-13 U Pantone. Petal color, outer base: P 56-4 U Pantone. Petal color, inner base: P 53-5 U Pantone Petal color, inner tip: P 26-16 U Pantone. Petal Color, Fully opened: Outer surface, near base: Near P 68-6 U Pantone. Outer surface, apex: Near P 68-7 U Pantone. Inner surface, near base: Near P 59-2-U Pantone. Inner surface, apex: Near P 59-7 U Pantone. Color Changes when Aging: Near P 59-14 U Pantone.

*Bud:* (*near opening*).—Shape: Conical. Length: Approximately 1.5 cm. Diameter: Approximately 0.9 cm. Color, Apex of Bud: Near P 97-9 U Pantone. Color, Base of Bud: Near P 57-12 U Pantone.

*Sepals*.—Color, Back of sepal: Near P 79-11 U Pantone. Color, Front of sepal: Near P 79-12 U Pantone.

*Pedicels*.—Length: Approximately 1 cm. Width: Approximately 0.3 cm. Aspect: Slightly spreading. Color: Near P 82-13 U Pantone.

*Fragrance*.—None detected.

REPRODUCTIVE ORGANS

Stamens: (Androecium).

*Number*.—Average 10.

*Filament length*.—Approximately 1.2 cm.

*Filament color*.—Near P 1-4 U Pantone.

*Anther length*.—0.3 cm.

*Anther color*.—Near P 22-15 U Pantone.

*Anther shape*.—Elliptic.

*Pollen color*.—Near P 7-4 U Pantone.

Pistil: (Gynoecium).

*Number*.—Average 5.

*Length*.—Approximately 1.3 cm.

*Style color*.—Near P 8-15 U Pantone.

*Stigma*.—Shape: Round. Color: Near P 74-15 U Pantone. Ovary Color: Near P 30-3 U Pantone.

OTHER CHARACTERISTICS

Temperature tolerance: Tolerates temperatures from approximately −2 degrees C. to 32 degrees C.

Disease/pest resistance: Increased resistance to normal diseases of *Echeveria*, in particular to *Rhizoctonia, Fusarium* and Powdery Mildew has been observed. Neither resistance nor susceptibility to normal pests of *Echeveria*, which include thrips and aphid has been observed.

Drought tolerance: Tolerates at least 3 weeks of high temperatures without supplemental water, showing no serious damage to plant.

What is claimed is:

1. A new and distinct cultivar of *Echeveria* plant named 'SAHARA' as herein illustrated and described.

* * * * *